United States Patent
Mohamed

(10) Patent No.: US 8,934,684 B2
(45) Date of Patent: Jan. 13, 2015

(54) METHOD AND SYSTEM FOR FACILITATING AN IMAGE GUIDED MEDICAL PROCEDURE

(75) Inventor: Ashraf Mohamed, Houston, TX (US)

(73) Assignee: Siemens Aktiengesellschaft, Munich (DE)

( * ) Notice: Subject to any disclaimer, the term of this patent is extended or adjusted under 35 U.S.C. 154(b) by 762 days.

(21) Appl. No.: 12/794,967

(22) Filed: Jun. 7, 2010

(65) Prior Publication Data

US 2011/0026786 A1 Feb. 3, 2011

Related U.S. Application Data

(60) Provisional application No. 61/230,130, filed on Jul. 31, 2009.

(51) Int. Cl.
*G06K 9/00* (2006.01)
*G06F 19/00* (2011.01)

(52) U.S. Cl.
CPC .......... *G06F 19/321* (2013.01); *G06F 19/3406* (2013.01)
USPC ....................................................... 382/128

(58) Field of Classification Search
None
See application file for complete search history.

(56) References Cited

U.S. PATENT DOCUMENTS

| | | | |
|---|---|---|---|
| 7,371,068 B2 * | 5/2008 | Lloyd et al. | 434/262 |
| 7,996,060 B2 * | 8/2011 | Trofimov et al. | 600/424 |
| 2004/0171924 A1 * | 9/2004 | Mire et al. | 600/407 |
| 2005/0027187 A1 * | 2/2005 | Barth et al. | 600/407 |
| 2005/0069205 A1 * | 3/2005 | Khomo | 382/187 |
| 2005/0108050 A1 * | 5/2005 | Knapheide | 705/2 |
| 2005/0177054 A1 * | 8/2005 | Yi et al. | 600/510 |
| 2006/0052690 A1 * | 3/2006 | Sirohey et al. | 600/420 |
| 2006/0111937 A1 * | 5/2006 | Yarger et al. | 705/2 |
| 2006/0225034 A1 * | 10/2006 | Peck et al. | 717/106 |
| 2006/0274885 A1 * | 12/2006 | Wang et al. | 378/65 |
| 2007/0055142 A1 * | 3/2007 | Webler | 600/425 |
| 2007/0073133 A1 * | 3/2007 | Schoenefeld | 600/407 |
| 2007/0073137 A1 * | 3/2007 | Schoenefeld | 600/407 |
| 2008/0081982 A1 * | 4/2008 | Simon et al. | 600/407 |
| 2008/0161680 A1 * | 7/2008 | von Jako et al. | 600/424 |
| 2008/0207997 A1 * | 8/2008 | Higgins et al. | 600/114 |
| 2008/0269599 A1 * | 10/2008 | Csavoy et al. | 600/426 |
| 2008/0269602 A1 * | 10/2008 | Csavoy et al. | 600/426 |
| 2008/0281181 A1 * | 11/2008 | Manzione et al. | 600/407 |
| 2009/0128553 A1 * | 5/2009 | Perry et al. | 345/419 |
| 2009/0171244 A1 * | 7/2009 | Ning et al. | 600/567 |
| 2009/0262894 A1 * | 10/2009 | Shukla et al. | 378/65 |
| 2009/0326336 A1 * | 12/2009 | Lemke et al. | 600/300 |

OTHER PUBLICATIONS

C. Karmonik et al. "Stent-Assisted Coiling of Intracranial Aneurysms Aided by Virtual Parent Artery Reconstruction,"Amercian Journal of Neuroradiology, 26:2368-2370, Oct. 2005.

(Continued)

*Primary Examiner* — Wenpeng Chen

(57) ABSTRACT

A method for facilitating an image guided medical procedure, utilizing images relating to the procedure, that includes performing a planning stage; performing an assessment stage; and performing an assessment stage via a unified workflow and user interface. The images relating to the procedure and extracted objects from the images are treated in the same manner so that image information from the stages may be combined for pre-, intra-, and post-procedural tasks.

20 Claims, 6 Drawing Sheets

(56) References Cited

OTHER PUBLICATIONS

G.P.Penney et al. Registration of Tomographic Images to X-ray Projections for Use in Image Guided Interventions Phd thesis,Univ. College London,CISG,Division of Radiological Sciences, Guy's Hospital, King's College London, London SE1 9RT England, 2000.

M.Groher et al. "Segmentation-driven 2D-3D Registration for Abdominal Catheter Intervention" Medical Image Computing and Computer Assisted Intervention (MICCAI 2007, Brisbane, Australia, Oct. 2007.

M.J. Wallace et al. "Three-Dimensional C-arm Cone-Beam CT: Applications in the Interventional Suite" J Vasc Interv Radiol, 19:799.813. 2008.

Virtual Endoscopy and Related 3D Techniques, Editors P. Rogalla, J. Terwisscha van Scheltinga and B. Hamm, published by Springer, Berlin, New York and London, 2001 and 2002.

Medical Image Registration, Edited by Joseph B. Hajnal, Derek L.G. Hill and David J. Hawkes in the Biomedical Engineering Series published by CRC Press, Boca Raton, London, New York and Washington, D.C., 2001.

Digital Image Processing, by Gonzalez and Woods, published by Prentice-Hall Inc., New Jersey, US, 2002.

Level Set Methods and Fast Marching Methods, by J.A. Sethian published by Cambridge University Press, 1996 and 1999.

Image Processing, Analysis, and Machine Vision, by Sonka, Hlavac, and Boyle, published by Brooks/Cole Publishing Company, Pacific Grove, California, 1999.

Insight Into Images, editor Terry S. Yoo, published by A K. Peters, Wellesley, Massachusetts, US, 2004.

Fundamentals of Electronic Image Processing, by A.R. Weeks, Jr., IEEE Press, New York, 1996.

\* cited by examiner

| ASSESSMENT STAGE |
|---|
| REGISTER AND FUSE PRE-PROCEDURAL WITH INTRA-PROCEDURAL AND POST-PROCEDURAL IMAGES |
| REGISTER AND FUSE SEGMENTED, SIMULATED, OR PLANNED ENTITIES WITH POST-PROCEDURAL IMAGES |
| BASED ON POST-PROCEDURAL IMAGES: |
| E.G. SEGMENT TREATED TUMOR |
| SEGMENT NEEDLE OR DEVICE |
| OTHER TASKS |

FIG. 1C

METHOD AND SYSTEM FOR FACILITATING AN IMAGE GUIDED MEDICAL PROCEDURE

CROSS-REFERENCE TO RELATED APPLICATION AND CLAIM OF PRIORITY

Specific reference is hereby made to copending U.S. Provisional Patent Application No. 61/230,130, filed Jul. 31, 2009 in the name of inventor Ashraf Mohamed and entitled "Generic Workflow and Software Architecture for Interventional Medical Procedures", and which is hereby incorporated herein by reference and whereof the benefit of priority is claimed.

FIELD OF THE INVENTION

The present invention relates generally to the field of medical imaging and more particularly to a method and system for facilitating an image guided medical procedure such as a procedure utilizing a generic workflow and software architecture for interventional medical procedures.

BACKGROUND OF THE INVENTION

An interventional medical procedure is typically a minimally invasive procedure performed under image guidance. Common interventional imaging methods include X-ray fluoroscopy, computer tomography (CT), ultrasound (US), and magnetic resonance imaging (MRI). Examples of interventional procedures typically include balloon angioplasty, lesion biopsy, chemoembolization, radiofrequency ablation and drain insertions.

During many types of interventional procedures, the physician relies on information not visible in intra-operative images, but is available in pre-operative images. For example, a thoracic lesion that is the target of a biopsy procedure may not be easily visible on ultrasound or X-ray fluoroscopy used during the intervention. However, the same lesion may be visible on pre-procedural diagnostic CT images. Therefore, there is great need for bringing pre-operative images into the interventional procedure room and in integrating or fusing the information that they present with the intra-procedural images.

Unless the context suggests otherwise, the terms post-procedural and post-operative are used herein interchangeably. In many procedures, there is also a need to assess the outcome of the procedure via post-procedural images. For example, positron emission tomography (PET) images acquired after the intervention may provide the physician with information on the efficacy of the embolization of a liver tumor. Therefore, such post-procedural images may need to be fused with pre-operative and intra-operative images for effective comparison and collective examination of the information presented in all these images simultaneously.

In the above-mentioned circumstances, for which there is a need to combine information from pre-operative, intra-operative, and post-operative images, solutions proposed in the prior art typically decouple the image registration and fusion tasks from other pre-, intra-, and post-procedural tasks. Thus, for example, software tools are available for segmenting and computing the volume of a liver tumor based on a pre-procedural CT, but a separate tool is used for registration and fusion of the same pre-procedural CT image with intra-procedural CT or US image. The use of multiple software tools during a single medical procedure, and the decoupling of technically required steps from clinical tasks, provide for a suboptimal workflow in many interventional procedures. Moreover, solutions in the prior art are generally not able to transfer objects associated with one image, such as a planned needle trajectory or the contour of a segmented tumor, across different images belonging to the same patient, for comparison, or for use in guiding the interventional procedure.

Various aspects relating generally to the background and field of the present invention are treated in a number of textbooks, in addition to the publications referred to in the course of the description of the present invention. For example, reference is made to the following text-books for background material which may be found useful: VIRTUAL ENDOSCOPY AND RELATED 3D TECHNIQUES, Editors P. Rogalla, J. Terwisscha van Schelting a, and B. Hamm, published by Springer, Berlin, N.Y., and London, 2001, 2002; MEDICAL IMAGE REGISTRATION, edited by Joseph B. Hajnal, Derek L. G. Hill, and David J. Hawkes in the Biomedical Engineering Series published by CRC Press, Boca Raton, London, New York and Washington, D.C., 2001; DIGITAL IMAGE PROCESSING, by Gonzalez and Woods, published by Prentice-Hall Inc., New Jersey, 2002; LEVEL SET METHODS AND FAST MARCHING METHODS, by J. A. Sethian, published by Cambridge University Press, 1996; 1999; IMAGE PROCESSING, ANALYSIS, AND MACHINE VISION, by Sonka, Hlavac, and Boyle, published by Brooks/Cole Publishing Company, Pacific Grove, Calif., 1999; INSIGHT INTO IMAGES, editor Terry S. Yoo, published by A K Peters, Wellesley Mass., 2004; and FUNDAMENTALS OF ELECTRONIC IMAGE PROCESSING, by A. R. Weeks, Jr., IEEE Press, New York, 1996; and various other text-books.

BRIEF SUMMARY OF THE INVENTION

In accordance with an aspect of the present invention, a method for facilitating an image guided medical procedure, utilizing images relating to the procedure, includes performing a planning stage, including: obtaining a plurality of pre-procedural images, registering and fusing together the plurality of pre-procedural images, and extracting entities, or data objects, based on the pre-procedural images; performing an intervention stage, including: obtaining intra-procedural images, registering and fusing the pre-procedural and intra-procedural images, registering and fusing the entities with the intra-procedural images, and segmenting selected ones of the entities, based on the intra-procedural images; and performing an assessment stage, including: obtaining post-procedural images, registering and fusing the pre-procedural, the intra-procedural, and the post-procedural images, registering and fusing the entities with the post-procedural images, segmenting selected ones of the entities based on the post-procedural images.

In accordance with another aspect of the invention, extracting the entities comprises any of segmenting an image area, segmenting a feature, segmenting a tumor, segmenting a treated tumor, segmenting a device, simulating a device, segmenting a vessel tree, planning a needle trajectory, tracking a needle position, and segmented, simulated, and planned entities, and similar items.

In accordance with another aspect of the present invention, a method for facilitating an image guided medical procedure, utilizing images relating to the procedure, includes performing a planning stage, including: obtaining a plurality of pre-procedural images, registering and fusing together the plurality of pre-procedural images, and extracting entities, or data objects, based on the pre-procedural images; for example, the extracting of entities can comprise segmenting a tumor, simulating a device, segmenting a vessel tree, planning a needle trajectory; the method comprises performing an intervention stage, including: obtaining intra-procedural images, registering and fusing the pre-procedural and intra-procedural images, registering and fusing the entities with the intra-procedural images, and segmenting selected ones of the entities, based on the intra-procedural images; for example, the extracting of entities can comprise segmenting a tumor, and tracking a needle position; and the method comprises performing an assessment stage, including: obtaining post-procedural images, registering and fusing the pre-procedural, the intra-procedural, and the post-procedural images, registering and fusing the entities with the post-procedural images, segmenting selected ones of the entities based on the post-procedural images; for example, segmenting a treated tumor and segmenting a needle or device.

In accordance with an aspect of the present invention, a method for facilitating an image guided medical procedure, utilizing images relating to the procedure comprises: supporting planning, intervention, and assessment stages of the procedure via a unified workflow and user interface (UI); making available data and images from one stage available to a subsequent stage, including fused images comprising data from a plurality of images from at least one stage; and providing guidance to or for a physician during a stage of the procedure by way of the UI.

In accordance with an aspect of the present invention, making available data and images includes making available data on fused images comprising data from a plurality of stages; and making available data on fused images comprising data from entities.

In accordance with an aspect of the present invention making available data and images includes: making available data on fused images comprising data from a plurality of stages; and making available data on fused images comprising data from entities including data from a plurality of stages.

In accordance with an aspect of the present invention, providing guidance for a physician comprises making available data derived from header information of a respective image.

In accordance with an aspect of the present invention providing guidance for a physician comprises utilizing a respective application assistant program to provide step by step guidance through tasks required in a specific clinical procedure.

In accordance with an aspect of the present invention a system for facilitating an image guided medical procedure, utilizing images relating to the procedure, comprises: a memory device for storing a program and other data; and a processor in communication with the memory device, the processor being operative with the program for:
  supporting planning, intervention, and assessment stages of the procedure via a unified workflow and user interface (UI);
  making available data and images from one stage available to a subsequent stage, including fused images comprising data from a plurality of images from at least one stage; and
  providing guidance for a physician during a stage of the procedure by way of the UI.

In accordance with an aspect of the present invention, a development tool for assisting an application developer by facilitating the design of an application assistant for a method for facilitating an image guided medical procedure, comprises:
  a computer program utilizing a graphical programming approach, and utilizing entered data, including data on:
    the type of images to be handled by the application assistant,
    tasks involved at steps of the method,
    pre-required conditions necessary before a stage of the method, and
    user mouse button clicks for identifying anatomical landmarks on an image associated with the method and being displayed on a workstation display monitor;
  presenting a plurality of views for each workflow step, including a user interface view and an action view, wherein:
    (a) the user interface view is utilized for defining user interface view components and a layout thereof as presented to a user, and
    (b) the action view of a workflow step defines preconditions to be met before the workflow step is begun, and inputs to the step from previous steps, including any and all of images, segmented structures, and necessary tasks to act on the input and like items; and
  wherein the user interface components defined in the user interface view provide triggers that invoke a service task to perform a required action.

In accordance with an aspect of the present invention, the user interface view components are of a type as may include push buttons, radio buttons and text boxes and the like; and the required action is of a type as may include a user button click on the user interface to trigger a registration service task to register an external MRI image to a real-time angiographic X-ray image, and like tasks.

BRIEF DESCRIPTION OF THE SEVERAL VIEWS OF THE DRAWING

The invention will be more fully understood from the detailed description following, in conjunction with the Drawing, in which.

DETAILED DESCRIPTION OF PREFERRED EMBODIMENTS OF THE INVENTION

Figure 1A:
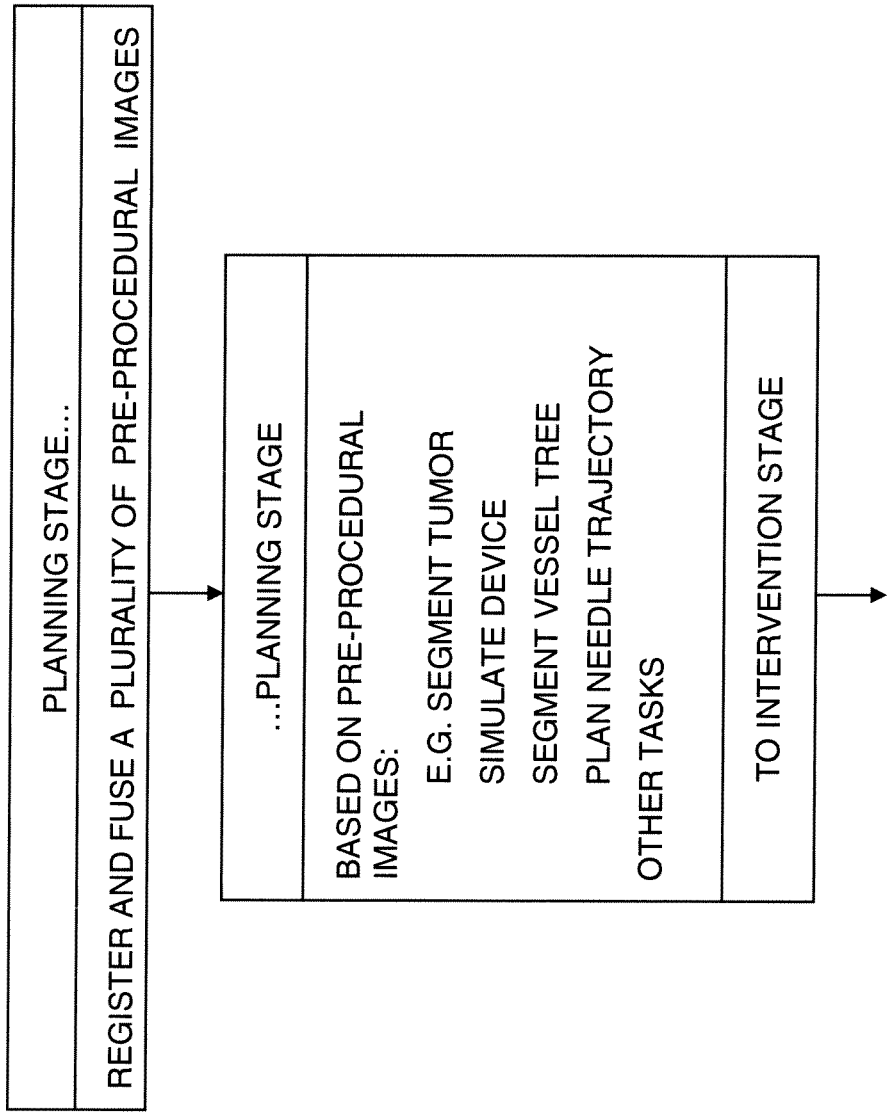
FIG. 1 (1A, 1B, and 1C) shows in chart form the three stages considered and steps relating thereto, in accordance with principles of the present invention.

As hereinabove stated, it is an object of the present invention to provide a system and method for a generic workflow and software architecture for streamlining the various steps and tasks required during an image-guided interventional medical procedure. The stages of the workflow generally follow the logical sequence of tasks required before, during, and after the intervention. The present invention provides a unified approach for interaction of the physician or other appropriate operator or user with pre-, post- and intra-procedural multimodality images. The tasks, images and data available for the physician depend on the current stage of the workflow. The approach includes a unified coordinate system for the grouping of all images am associated data needed during pre-, intra-, post- procedural images. For example, medical procedures benefiting from this approach include liver tumor embolization procedures and abdominal aortic aneurysm treatments.

In the current invention, the three principal stages of an interventional procedure are recognized and the present invention guides the physician and/or other user as may be appropriate, in performing the tasks required during each of these stages through a unified and streamlined user interface. These three principal stages are as follows: pre-procedural planning of the intervention, performing the actual intervention, and post-procedural assessment. Images and any extracted, simulated, or planned entities, such as a segmented tumor contour or a simulated device, are treated in unified fashion. That is to say, both images and extracted entities are treated as similar type objects that can be registered and fused on the display of the interventional computer workstation. A single coordinate system is used for all three-dimensional (3D) images and entities needed throughout the three stages. At any point in time, a set of possible tasks is available to the physician or user. These tasks depend on the stage of the intervention, attributes of images or entities, and the state of the software application, which is also dependent on previously performed tasks. The software provides guidance to the physician or user as to which tasks are possible at any given point in time. This provides a streamlined and controlled workflow, which reduces the time an interventional procedure may take, and improves usability of the software.

In accordance with preferred embodiments thereof, the present invention provides advantages over prior art methods, including the following: a unified workflow that combines all three stages of an interventional procedure; an overall coordinate system for all 3D images and entities extracted from or created based on these images; and a unified approach and software architecture for fusion and visualization of images and all entities extracted from or created, based on these images.

As concerns a unified workflow for all stages or phases of an interventional procedure in accordance with principles of the present invention, FIG. 1 illustrates three stages of a typical exemplary interventional medical procedure and exemplary image-driven tasks that are needed by the performing physician at each of these stages. The current invention supports all three stages of the intervention via a unified workflow and user interface (UI). The resulting data and images from one stage are available to the subsequent stages. The UI of the invention guides the physician during each stage of the intervention and allows for a streamlined and logical flow of image and other data or information.

FIG. 1A shows the planning stage wherein a plurality of pre-procedural images are registered and fused. Still in the planning stage, FIG. 1A shows procedures based on the pre-procedural images, such as, for example, segmenting a tumor, simulating a device, and segmenting a vessel tree. Other tasks, not herein enumerated may also be addressed.

Figure 1B:
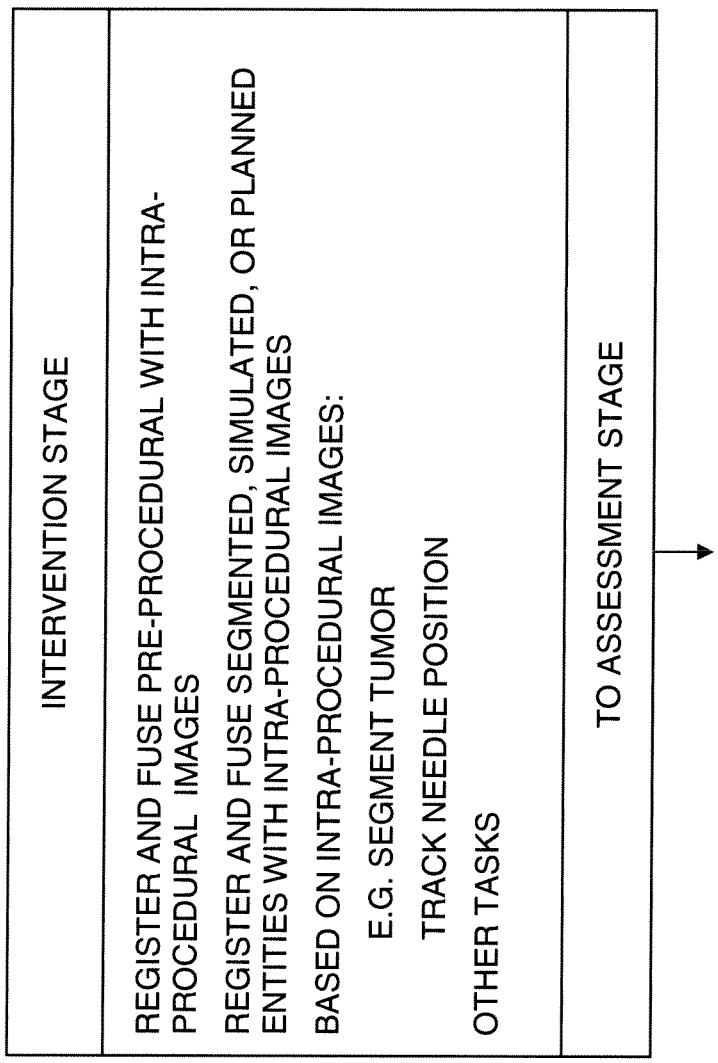

FIG. 1B shows that in the intervention stage, pre-procedural images are registered and fused with intra-procedural images. Also in this intervention stage, segmented, simulated, or planned entity images are registered and fused with intra-procedural images. Tasks based on intra-procedural images that may be performed include, for example, segmenting the tumor, tracking a needle position, and other tasks not herein enumerated.

FIG. 1C shows the assessment stage, in which pre-procedural images are registered and fused with intra-procedural and post-procedural images. Also in this assessment stage, segmented, simulated, or planned entities may be registered with post-procedural images. Tasks based on post-procedural images that may be performed include, for example, segmenting the treated tumor, segmenting a needle or a device, and other tasks, not herein enumerated.

In accordance with an embodiment of the invention, the following steps are generally applicable.

Planning associated with the procedure generally includes registering and fusing pre-procedural images based on pre-procedural images; segmenting, for example, an image of a tumor; simulating a device as may be utilized in the procedure; segmenting a vessel tree; planning a needle trajectory. Intervention associated with a procedure generally includes registering and fusing pre-procedural with intra-procedural images; registering and fusing segmented, simulated and/or planned entities with intra-procedural images, as based, for example, on intra-procedural images; segmenting for example, a tumor; tracking a needle position; and performing an assessment of the procedure.

The assessment generally includes registering and fusing pre-procedural, with intra-procedural and post-procedural images; registering and fusing segmented, simulated or planned entities with post-procedural images, generally based on post-procedural images; segmenting a treated tumor; and segmenting the device needle.

In reference to the user interface, it is noted that FIGS. 1A, 1B, and 1C illustrates an example of tasks performed by the physician during the three stages, planning, intervention, and assessment of an exemplary interventional medical procedure. The user interface in accordance with principles of the present invention is organized around these three stages, and it makes a number of tasks available during each stage. The available tasks depend on previously performed tasks, the modality of the loaded image or images, and the part of the body visible in these images. Such information about the images is available in the respective DICOM$^{SM}$ header of the loaded images.

DICOM$^{SM}$ is a service mark corresponding to Digital Imaging and Communications in Medicine, which is an industry standard for transferring radiological images and other medical information between computers. Stated to be patterned after the Open System Interconnection of the International Standards Organization, DICOM$^{SM}$ is stated to enable digital communication between diagnostic and therapeutic equipment and systems from various manufacturers.

In accordance with the present invention, the use of a single and streamlined user interface for the different stages of an interventional medical procedure makes it possible for software modules to share various image and data components in an efficient manner. Each of these software modules may perform a specific task during one or more of the stages of the intervention. The result of each task performed is available for other software modules as described below.

During the planning stage, the physician relies on pre-procedural images to perform planning tasks such as the segmentation of the target lesion, selection of the devices and instruments to be used during the intervention, and a comparison of a lesion size in between a number of pre-operative images. See, for example, C. Kaimonik, C. M. Strother, X. Chen, F. Deinzer, R. Kluznik, M. E. Mawad, "Stent-Assisted Coiling of Intracranial Aneurysms Aided by Virtual Parent Artery Reconstruction," American Journal of Neuroradiology, 26:2368-2370, October 2005. For example, in a transarterial chemoembolization (TACE) of a liver tumor, based on a CTA image, the physician may extract the vessel tree of the hepatic artery starting from the main hepatic artery to the arterial branch feeding the target tumor. See, for example, G.

P. Penney, "Registration of Tomographic Images to X-ray Projections for Use in Image Guided Interventions," Phd thesis, University College London, CISG, Division of Radiological Sciences, Guy's Hospital, King's College London, London SE1 9RT England, 2000; M. Groher, F. Bender, R-T Hoffmann, N. Navab, "Segmentation-driven 2D-3D Registration for Abdominal Catheter Intervention," Medical Image Computing and Computer Assisted Intervention (MICCAI 2007), Brisbane, Australia, October 2007; and M. J. Wallace, M. D. Kuo, C. Glaiberman, C. Binkert, R. C. Orth, G. Soulez, "Three-Dimensional C-arm Cone-bean CT: Applications in the Interventional Suite," J Vasc Intery Radiol, 19:799:813, 2008. The contents of the publications in the present paragraph are hereby incorporated herein by reference to the extent not incompatible with the present invention.

The physician may also use a CT image to segment the tumor, compute its volume, and understand its position in relation to neighboring tissues.

During the intervention stage, the physician uses the planning information for guidance and accurate navigation of medical devices or instruments. For example, during a TACE procedure, the physician navigates a catheter under X-ray fluoroscopic guidance from the common hepatic artery towards the arterial branch feeding the tumor to be embolized. In perfoiming this task, the physician may rely on a 3D roadmap image based on the segmented arterial tree from a pre-operative CTA image. See the afore-mentioned publication by Groher et al. The present invention allows this segmented arterial tree to be shared by and directly available for the software module that performs the overlay on 2D fluoroscopic images.

During the assessment stage, the physician may rely on post-procedural images to assess the accuracy and efficacy of the intervention or other administered form of treatment. For example, the physician may use post-TACE CT or C-arm CT images to visualize the embolized portion of a tumor. A segmentation algorithm may be used to extract and compute the volume of the embolized portion of the tumor and compare it to the whole tumor as segmented from a pre-procedural CT image.

In order to guide the physician during various stages of the intervention, an embodiment of the present invention uses a pre-defined software module for each clinical application. Each of these software modules is called an "Application Assistant". The Application Assistant provides text messages and guidance hints to the physician(s) indicating which tasks are permissible at each point in time during a medical procedure. For example, one Application Assistant may be used to guide the physician in a step-by-step fashion through all tasks of an Abdominal Aortic Aneurysm (AAA) treatment. For a further example, another Application Assistant may be used for organizing the workflow and various tasks required during a TACE of a liver tumor.

A benefit of the architecture of the current invention is that creating a new Application Assistant is a simple task for a software application developer. The application developer needs to specify the type of images that the application handles, the tasks involved at each step of the application, and pre-required conditions necessary before each stage or step of the medical procedure. Each Application Assistant is represented by a lightweight computer configuration file that may be created via a Development Tool. The Development Tool that assists the developer in creating the Application Assistant file is conceived as a part of the current invention.

Figure 2:
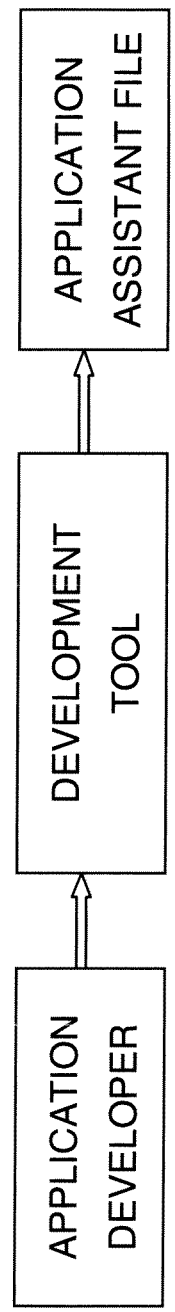
FIG. 2 shows in block diagrammatic form the utilization of a development tool for generating an Application Assistant file, in accordance with principles of the present invention.

The role of the development tool (DT) is to assist the developer of the application (AD) to generate the Application Assistant file (AAF) through an easy to use graphical programming approach. FIG. 2 shows a block diagram with an Application Developer utilizing a Development Tool DT to generate a light weight Application Assistant File AAF that defines the developed computer application.

For each of the afore-mentioned three stages of an interventional procedure, the DT allows the AD to define a number of clinical workflow steps that must be performed in sequence by the user of the software application. An example of a clinical workflow step is the acquisition of an angiographic image with certain characteristics. Another example is the user interaction with the application, for example, a user click of a mouse button, in order to identify a certain anatomical landmark on an image visible on the workstation's display monitor.

Figure 3:
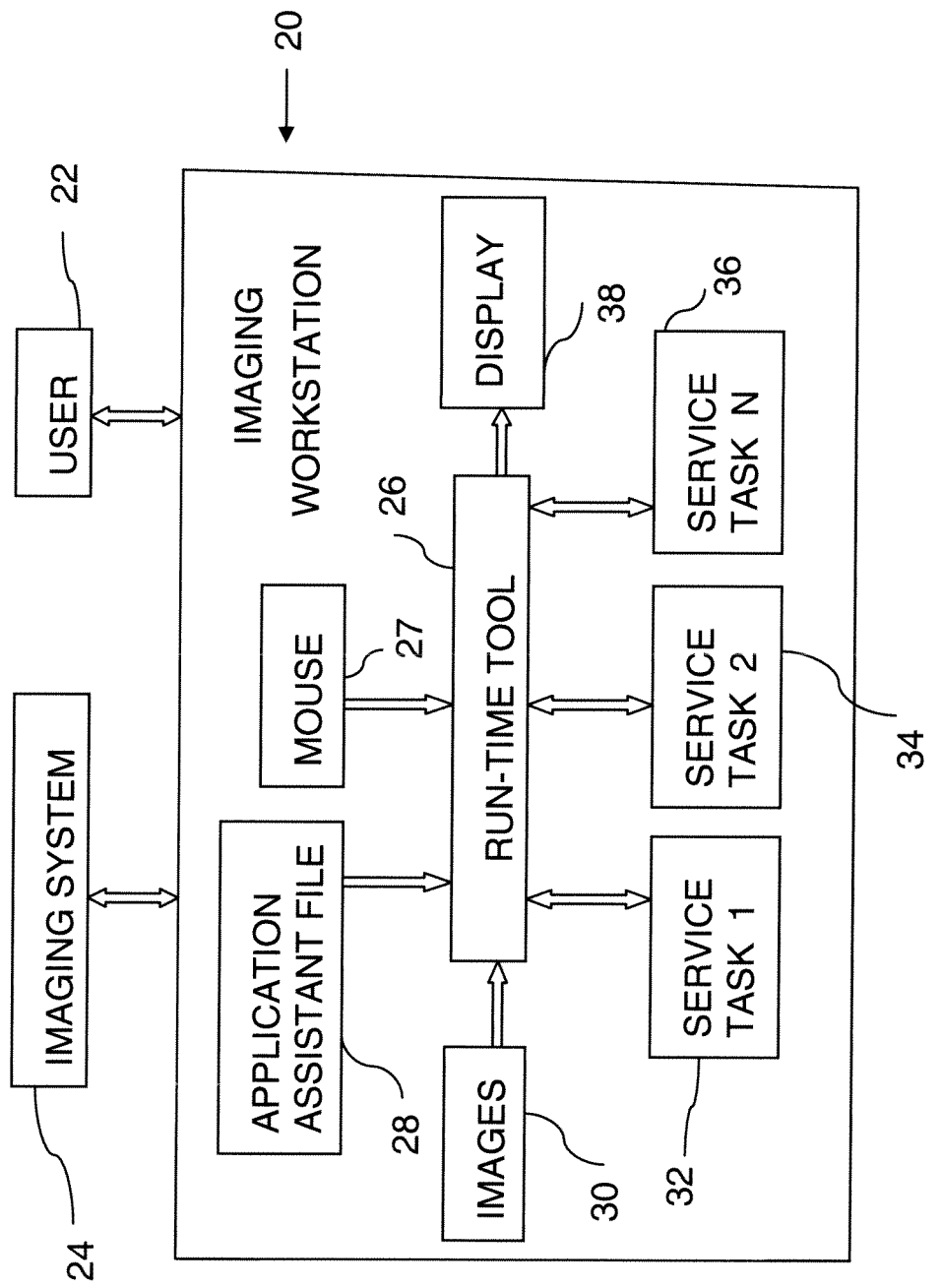
FIG. 3 shows in block diagrammatic form components in accordance with principles of the present invention incorporated into an imaging workstation.

The block diagram in FIG. 3 shows an overview in accordance with principles of the present invention in which a workstation 20 is utilized by a User 22. An Imaging System 24 is coupled for two-way data interchange with Workstation 20. In Imaging Workstation 20, the Run-time Tool (RT) 26 receives inputs from the Application Assistant File 28, a user mouse 27, and images 30. The RT is coupled to a display 38 and to a number of Service Task functionalities, 32, 34, and 26, numbered as Service Tasks 1, 2, . . . N.

The role of the run-time tool (RT) is to translate the actions and UI components defined in the AAF into real-time behavior to be experienced by the user of the software application. Generally, in clinical environments, each radiographic system such as, for example, an X-ray arm machine, will typically have a clinical workstation associated with it. The workstation is used by the physician or other operator to review various images, fuse images, plan a certain procedure, and so forth. The RT preferably resides on the workstation of the radiographic interventional system and manages the communication with the different components of the workstation, including local image stores, display, pointing devices, and service tasks. The AAF is used by the RT to define interaction between the user and the interventional imaging system, service tasks running on the imaging system's workstation, and other resources.

In accordance with an exemplary embodiment of the present invention, the DT provides the AD with two views of each workflow step—a user interface view (UIV), and an Action View (AV). The UIV is used by the developer in order to define the UI components, for example, push buttons, radio buttons, and text boxes, and their layout as they are presented to the user. In the AV of the workflow step, the AD defines preconditions that must be met before this step is possible, the inputs to this step from previous steps, for example, images or segmented structures, and the necessary tasks that act on these inputs. The UI components which are defined in the UIV provide triggers that invoke a service task to perform the required action. For example, a click by the user on a button on the UI, triggers a registration service task to register and external MRI image to a real-time angiographic X-ray image.

As concerns an overall coordinate system for all 3D images and entities extracted or created based on these images, in accordance with an embodiment of the present invention, the invention utilizes the coordinate system of one 3D image as a reference coordinate system for all images and associated entities. Hereinafter, this image will be called the reference 3D image.

Only one image can act as the reference 3D image. In one embodiment of the invention, the reference 3D image is the last loaded 3D image. If a previously loaded 3D image is again loaded, this functions as an update, that is, this now becomes the new reference 3D image. For each new 3D image dataset to be loaded, 3D/3D registration with the latest image already loaded is performed. Therefore, a 3D/3D registration is available between each pair of images loaded. The user may select a rigid or non-rigid registration algorithm from a variety of algorithms already known in the art for intra- and inter-modality 3D/3D image registration. Manual 3D/3D image registration is also supported.

If 3D images must be fused with 2D intra-procedural images, a 2D/3D registration must be available between the reference image and the 2D images. Various approaches for obtaining this 2D/3D registration are described in the prior art; see the aforementioned publications by Penney and by Groher. The present invention is transparent to the manner in which the 2D/3D registration is obtained or updated.

With regard to a unified approach and software architecture for fusion and visualization of images and all entities extracted from or created based on these images, depending on the modality, acquisition protocol, and body region visible in the images, each 2D or 3D image may allow a number of tasks to be performed. Each such task will hereinafter be called a "Service Task". A Service Task operates on one or more images to produce as a result another image or a representation of a real or virtual entity. For example, during the planning stage of an intervention, the vessel tree or a tumor may be segmented from a CTA dataset and subsequently used during the procedure for guiding the intervention. In another example, the entry point and the trajectory of a needle used for a biopsy procedure may be planned on a pre-procedural CT image where the biopsy target is visible. In a third example, a device such as a stent or a filter may be planned based on pre-operative images by simulating the deployed device and fusing it with the available pre-operative images. See, for example, the aforementioned publication by Karmonik et al.

Let extracted objects, such as for example, a segmented tumor, simulated objects, such as for example, a simulated stent or IVC filter, or electronic markings, such as for example, a planned needle trajectory, based on 2D or 3D images be termed "entities". The present invention treats images and entities extracted from these images in the same manner, that is, both as "data objects" having a number of associated attributes. Images and entities may differ in the value of the associated attributes. The attributes control the way in which images and entities are displayed, manipulated, and used by different service tasks. For example, an attribute controls the color palette selected for the display of the associated image or entity. Attributes also control the reference coordinate system associated with a data object.

With images and entities treated in a similar fashion, software modules can easily compare, fuse and visualize both types of data objects. For example, the present invention makes it possible to compare and visualize post stent placement C-arm CT in an aneurysm embolization procedure to the pre-procedural plan of virtual stent.

Where information and data are referred to herein as being provided to or for the physician, naturally this will be broadly understood to include its being provided to or for other users, operators, and personnel as may be appropriate. The same applies to tasks referred to as being performed by the physician.

The present invention has a considerable number of applications over an extensive field. Virtually all image-guided interventional medical procedures can benefit from this invention. Examples of potential applications include trans-arterial chemoembolization of liver tumors, and Abdominal Aortic Aneurysm treatments.

Figure 4:
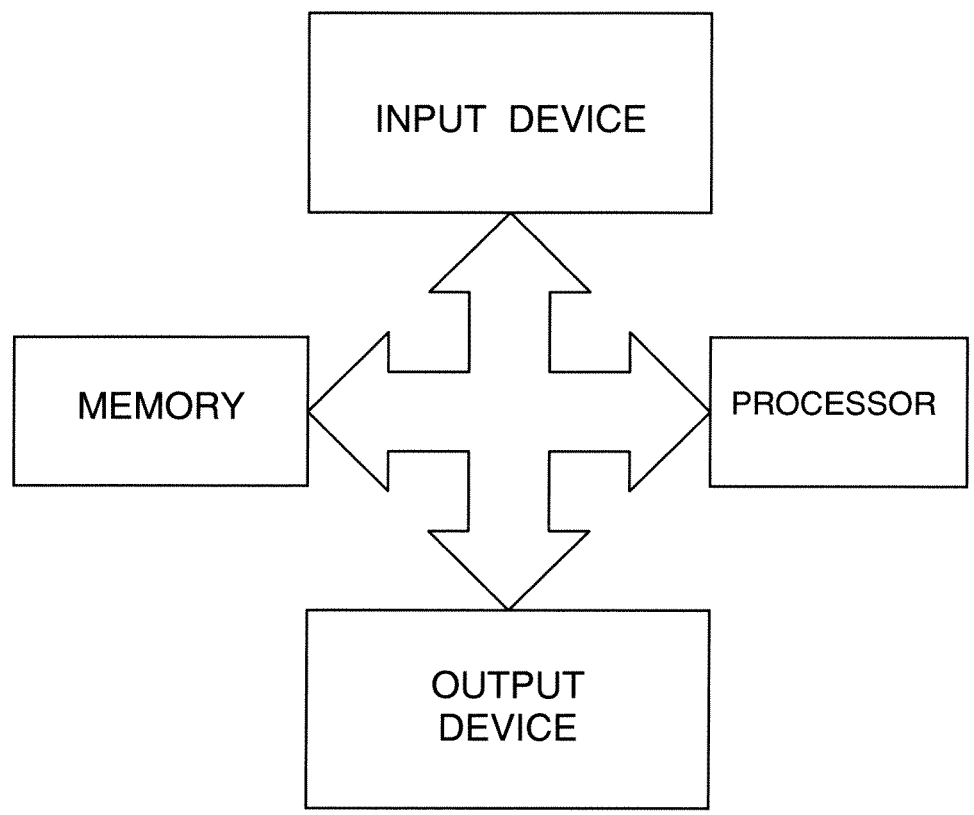
FIG. 4 shows in a generalized basic schematic as may be utilized for implementing steps of the invention, including a digital processor coupled for two way data communication with an input device, an output device, and a memory device for storing a program and other data, which is preferably comprised in a workstation of a radiographic system.

As has been explained in referenced to a preferred embodiment, the present invention is preferably implemented and runs on the workstation of the radiographic system. Thus, the RT resides on the workstation while the development tool can be run on a regular computer or a workstation. As will be apparent, if need be, the present invention could also be implemented with the use and application of imaging equipment in conjunction with a programmed digital computer. FIG. 4 shows a generalized configuration in basic schematic form in which appropriate digital processing means, which preferably may be part of a workstation, is coupled for two way data communication with an input device, an output device, and a memory device for storing a program and other data. The input device is so designated in broad terms as a device for providing an appropriate image or images for processing in accordance with the present invention and having provision for user interaction and control, including the use of a computer mouse. For example, the input may be from an imaging device, such as a device incorporated in a CATSCAN, X-ray machine, an MRI or other device, or a stored image, or by communication with another computer or device by way of direct connection, a modulated infrared beam, radio, land line, facsimile, or satellite as, for example, by way of the World Wide Web or Internet, or any other appropriate source of such data.

The processor is operative with a program set up in accordance with the present invention for implementing steps of the invention. Such a programmed computer may interface readily through communications media such as land line, radio, the Internet, and so forth for image data acquisition and transmission.

Images may be outputted directly, or by way of storage, or communication with another computer or device by way of direct connection, a modulated infrared beam, radio, land line, facsimile, or satellite as, for example, by way of the World Wide Web or Internet, or any other appropriate processor of such data. The image output device may include a computer type display device using any suitable apparatus such as a cathode-ray kinescope tube, a plasma display, liquid crystal display, and so forth, or it may include memory for storing an image for further processing, or for viewing, or evaluation, as may be convenient, or it may utilize a connection or coupling including such as are noted above in relation to the input.

The invention may be readily implemented, at least in part, in a software memory device and packaged in that form as a software product. This can be in the form of a computer program product comprising a computer useable medium having computer program logic recorded thereon for program code for performing the method of the present invention.

The present invention has also been explained in part by way of examples using illustrative exemplary embodiments. It will be understood that the description by way of exemplary embodiments is not intended to be limiting and that, while the present invention is broadly applicable, it is helpful to also illustrate its principles by way of exemplary embodiments without loss of generality.

It will also be understood that various changes and substitutions not necessarily herein explicitly described may be made by one of skill in the art to which it pertains. Such changes and substitutions may be made without departing from the spirit and scope of the invention which is defined by the claims following.

What is claimed is:

1. A method for facilitating an image guided medical procedure, comprising:
   performing a planning stage, comprising tasks of:
      obtaining a plurality of pre-procedural images,
      registering and fusing together said plurality of pre-procedural images, and extracting or creating entities, based on said pre-procedural images;
performing an intervention stage, comprising tasks of:
  obtaining intra-procedural images,
  registering and fusing said pre-procedural and intra-procedural images,
  registering and fusing said entities with said intra-procedural images, and
  segmenting selected ones of said entities, based on said intra-procedural images;
performing an assessment stage, comprising tasks of:
  obtaining post-procedural images,
  registering and fusing said pre-procedural, said intra-procedural, and said post-procedural images,
  registering and fusing said entities with said post-procedural images, and
  segmenting selected ones of said entities based on said post-procedural images;
determining an availability of a task during each respective stage depending on previously performed tasks, a modality of at least one obtained image, and a respective anatomical region shown in said at least one obtained image; and
providing information on operation and the availability of a task during each respective stage to a user,
wherein said images and said entities are treated in a unified manner as data objects that enables said images and said entities to be registered and fused in a respective task,
wherein said images comprise a plurality of associated attributes,
wherein said entities comprise a plurality of different associated attributes,
wherein the plurality of associated attributes of said images and the plurality of different associated attributes of said entities differ in values, and
wherein the plurality of associated attributes of said images and the plurality of different associated attributes of said entities control a way in which said images and said entities are displayed, manipulated, and used by the respective task.

2. The method for facilitating an image guided medical procedure as recited in claim 1, wherein said extracting or creating entities includes any of segmenting an image area, segmenting a feature, segmenting a tumor, segmenting a treated tumor, segmenting a device, simulating a device, segmenting a vessel tree, planning a needle trajectory, and tracking a needle position.

3. The method for facilitating an image guided medical procedure as recited in claim 1, further comprising utilizing an application assistant computer software program to provide to a user information on the operation and availability of a task during a respective stage, said program being generated by utilizing a particular development tool adapted therefore.

4. The method for facilitating an image guided medical procedure as recited in claim 1, further comprising obtaining information regarding said at least one obtained image from a respective header associated with said at least one obtained image.

5. The method for facilitating an image guided medical procedure as recited in claim 1, further comprising utilizing a single user interface for the performing steps of said planning, intervention, and assessment stages to assist planning, intervention, and assessment stages to assist images, task results, and other data to be shared among the respective tasks of the stages.

6. The method for facilitating an image guided medical procedure as recited in claim 5, further comprising:
  developing an application assistant computer software program for facilitating said image guided medical procedure by utilizing a computer software program operating on data, said data comprising data of:
    types of images to be handled by said application assistant,
    tasks involved at respective stages, and
    pre-required conditions necessary before performing a respective task; and
  running said application assistant computer software program for facilitating said image guided medical procedure.

7. The method for facilitating an image guided medical procedure as recited in claim 6, wherein said utilizing a computer software program operating on data comprises:
  defining user interface software components that permits the user to execute an action as part of carrying out a respective task or an associated sub-task; and
  defining pre-required conditions, inputs, and actions on said inputs of a respective task or an associated sub-task.

8. The method for facilitating an image guided medical procedure as recited in claim 6, wherein a respective application assistant makes said data and images from a respective stage available to a subsequently-performed stage, including fused images comprising data from a plurality of images from at least one stage, and provides guidance for the user on the operation and availability of a particular task during a respective stage by way of said user interface.

9. The method for facilitating an image guided medical procedure as recited in claim 8, wherein said guidance for the user comprises making available data derived from header information of a respective obtained image.

10. The method for facilitating an image guided medical procedure as recited in claim 8, wherein said guidance for the user comprises providing step by step guidance through tasks required in a specific clinical medical procedure.

11. The method for facilitating an image guided medical procedure as recited in claim 1, further comprising facilitating images, task results, and other data to be shared among the respective tasks of the stages.

12. A method for facilitating an image guided medical procedure, utilizing images relating to said procedure, comprising:
  supporting planning, intervention, and assessment stages of said procedure via a unified image-related workflow and a user interface, each respective stage comprising a plurality of tasks, a unified image being comprised of an image or extracted, simulated, or planned image object treated with all other images and image objects in a unified manner as data objects that enables said images and said image objects to be registered and fused in a respective stage;
  making data, images, and image objects from a respective stage available to a subsequent stage, including fused images comprising data from a plurality of images from at least one stage;
  determining an availability of a task during each respective stage depending on previously performed tasks, a modality of at least one obtained image, and a respective anatomical region shown in said at least one obtained image; and
  providing guidance for a user during each respective stage of said procedure on operation and the availability of a task by way of said user interface, wherein said images comprise a plurality of associated attributes, wherein said entities comprise a plurality of different associated attributes, wherein the plurality of associated attributes of said images and the plurality of different associated attributes of said entities differ in values, and wherein the plurality of associated attributes of said images and the plurality of different associated attributes of said entities control a way in which said images and said entities are displayed, manipulated, and used by the respective task.

13. The method as recited in claim 12, wherein said making data, images and image objects comprises:
making available data on fused images comprising data from a plurality of images from a plurality of stages; and
making available data on fused images comprising data from image objects.

14. The method as recited in claim 12, wherein said making data, images and image objects comprises:
making available data on fused images comprising data from a plurality of images from a plurality of stages; and
making available data on fused images comprising data from image objects including data from a plurality of stages.

15. The method as recited in claim 12, wherein said providing guidance for the user comprises making available data derived from header information of a respective image.

16. The method as recited in claim 15, wherein said providing guidance for the user comprises utilizing a respective application assistant computer software program to provide step by step guidance through tasks required in a specific clinical procedure.

17. A system for facilitating an image guided medical procedure, utilizing images relating to said procedure, comprising:
a memory device for storing a program and other data; and
a processor in communication with said memory device, said processor being operative with said program for:
supporting planning, intervention, and assessment stages of said procedure via a unified image-related workflow and a user interface, each respective stage comprising a plurality of tasks, a unified image being comprised of an image or extracted, simulated, or planned image object treated with all other images and image objects in a unified manner as data objects that enables said images and said image objects to be registered and fused in a respective stage;
making data, images, and image objects from a respective stage available to a subsequent stage, including fused images comprising data from a plurality of images from at least one stage;
determining an availability of a task during each respective stage depending on previously performed tasks, a modality of at least one obtained image, and a respective anatomical region shown in said at least one obtained image; and
providing guidance for a user during each respective stage of said procedure on operation and the availability of a task by way of said user interface,
wherein said images comprise a plurality of associated attributes,
wherein said entities comprise a plurality of different associated attributes,
wherein the plurality of associated attributes of said images and the plurality of different associated attributes of said entities differ in values, and
wherein the plurality of associated attributes of said images and the plurality of different associated attributes of said entities control a way in which said images and said entities are displayed, manipulated, and used by the respective task.

18. A method for facilitating an image guided medical procedure, comprising:
treating images obtained during pre-procedural, intra-procedural, and post-procedural stages of the procedure and entities either simulated, or extracted or created from said images as data objects;
establishing a single coordinate system for said data objects;
performing tasks of registration and fusion of said data objects in a coupled manner with other image-related tasks operating said data objects during each of the pre-procedural, intra-procedural, and post-procedural stages;
determining an availability of a task during each respective stage depending on previously performed tasks, a modality of at least one obtained image, and a respective anatomical region shown in said at least one obtained image; and
providing, during each respective stage, image information that combines results of the performing step carried out during a respective stage and any stage preceding said respective stage and the availability of a task during a respective stage to a user,
wherein said images comprise a plurality of associated attributes,
wherein said entities comprise a plurality of different associated attributes,
wherein the plurality of associated attributes of said images and the plurality of different associated attributes of said entities differ in values, and
wherein the plurality of associated attributes of said images and the plurality of different associated attributes of said entities control a way in which said images and said entities are displayed, manipulated, and used by the respective task.

19. A non-transitory computer medium embodied a computer program for performing method steps comprising:
performing a planning stage, comprising tasks of:
obtaining a plurality of pre-procedural images,
registering and fusing together said plurality of pre-procedural images, and
extracting or creating entities, based on said pre-procedural images;
performing an intervention stage, comprising tasks of:
obtaining intra-procedural images,
registering and fusing said pre-procedural and intra-procedural images,
registering and fusing said entities with said intra-procedural images, and
segmenting selected ones of said entities, based on said intra-procedural images;
performing an assessment stage, comprising tasks of:
obtaining post-procedural images,
registering and fusing said pre-procedural, said intra-procedural, and said post-procedural images,
registering and fusing said entities with said post-procedural images, and
segmenting selected ones of said entities based on said post-procedural images;
determining an availability of a task during each respective stage depending on previously performed tasks, a modality of at least one obtained image, and a respective anatomical region shown in said at least one obtained image;

providing information on operation and the availability of a task during each respective stage to a user; and presenting a plurality of views for each of the method steps comprising a user interface view and an action view, wherein said images and said entities are treated in a unified manner as data objects that enables said images and said entities to be registered and fused in a respective task, wherein said images comprise a plurality of associated attributes, wherein said entities comprise a plurality of different associated attributes, wherein the plurality of associated attributes of said images and the plurality of different associated attributes of said entities differ in values, wherein the plurality of associated attributes of said images and the plurality of different associated attributes of said entities control a way in which said images and said entities are displayed, manipulated, and used by the respective task, wherein the user interface view presents a layout to the user via a user interface view component, and wherein the action view presents preconditions to be met before performing said each of the method steps and inputs from previous method steps.

20. The non-transitory computer medium as recited in claim 19, wherein said user interface view component is selected from the group consisting of: a push button, a radio button, and a text box, wherein said user interface view component is clicked by the user for triggering a service task, and wherein the service task comprises a registration service task to register an external MRI image to a real-time angiographic X-ray image.

* * * * *